(12) United States Patent
Brambilla et al.

(10) Patent No.: US 8,763,618 B2
(45) Date of Patent: Jul. 1, 2014

(54) DOMESTIC APPLIANCE

(75) Inventors: Enrico Brambilla, Milan (IT); Fredrik Dellby, Alvsjo (SE)

(73) Assignee: Electrolux Home Products Corporation N.V., Zaventem (BE)

( * ) Notice: Subject to any disclaimer, the term of this patent is extended or adjusted under 35 U.S.C. 154(b) by 463 days.

(21) Appl. No.: 10/597,485

(22) PCT Filed: Apr. 26, 2006

(86) PCT No.: PCT/EP2006/003850
§ 371 (c)(1),
(2), (4) Date: Jul. 27, 2006

(87) PCT Pub. No.: WO2006/117110
PCT Pub. Date: Nov. 9, 2006

(65) Prior Publication Data
US 2008/0248075 A1    Oct. 9, 2008

(30) Foreign Application Priority Data

May 4, 2005    (EP) .................................. 05 009 754

(51) Int. Cl.
*B08B 3/00* (2006.01)

(52) U.S. Cl.
USPC ......................................... 134/110; 134/58 D

(58) Field of Classification Search
USPC ...................... 134/56 D, 57 D, 58 D, 93, 110
See application file for complete search history.

(56) References Cited

U.S. PATENT DOCUMENTS

| 2,245,737 | A | | 3/1938 | Tandberg et al. |
| 4,998,548 | A | | 3/1991 | Lagerstrand |
| 5,450,868 | A | * | 9/1995 | Young, Jr. ..................... 134/111 |
| 6,187,456 | B1 | | 2/2001 | Lever |
| 2001/0000097 | A1 | | 4/2001 | Nickell et al. |
| 2003/0213704 | A1 | | 11/2003 | Scheper et al. |
| 2004/0007253 | A1 | * | 1/2004 | Jung et al. ........................ 134/10 |
| 2004/0159337 | A1 | * | 8/2004 | Johnson et al. ................. 134/18 |
| 2005/0150528 | A1 | * | 7/2005 | Kim .............................. 134/108 |

FOREIGN PATENT DOCUMENTS

| EP | 0 270 129 A2 | 6/1988 |
| EP | 0 288 063 A2 | 10/1988 |
| EP | 0461870 | 12/1991 |
| EP | 1386575 A1 * | 2/2004 |
| EP | 1 415 585 A1 | 5/2004 |
| EP | 1 550 396 A2 | 7/2005 |
| GB | 712598 | 7/1954 |
| GB | 736024 | 8/1955 |
| JP | 04357916 | 12/1992 |
| JP | 5-111451 | 5/1993 |
| JP | 10-276960 | 10/1998 |
| JP | 2000-51136 | 2/2000 |
| JP | 2002315716 | 10/2002 |
| JP | 2004-254929 | 9/2004 |
| KR | 10-20040063270 | 7/2004 |
| WO | 9629924 | 10/1996 |
| WO | WO 99/47595 | 9/1999 |
| WO | WO 00/64259 | 11/2000 |
| WO | WO 01-93740 A1 | 12/2001 |
| WO | 0209779 | 2/2002 |
| WO | WO 02/40180 A1 | 5/2002 |

* cited by examiner

*Primary Examiner* — David Cormier
(74) *Attorney, Agent, or Firm* — Pearne & Gordon LLP

(57) ABSTRACT

The liquid-bearing domestic appliance, in particular domestic dishwasher, is provided with at least one antibiotic agent, in particular in the sump and/or the tub and/or an insert.

15 Claims, 3 Drawing Sheets

DOMESTIC APPLIANCE

Figure 1:
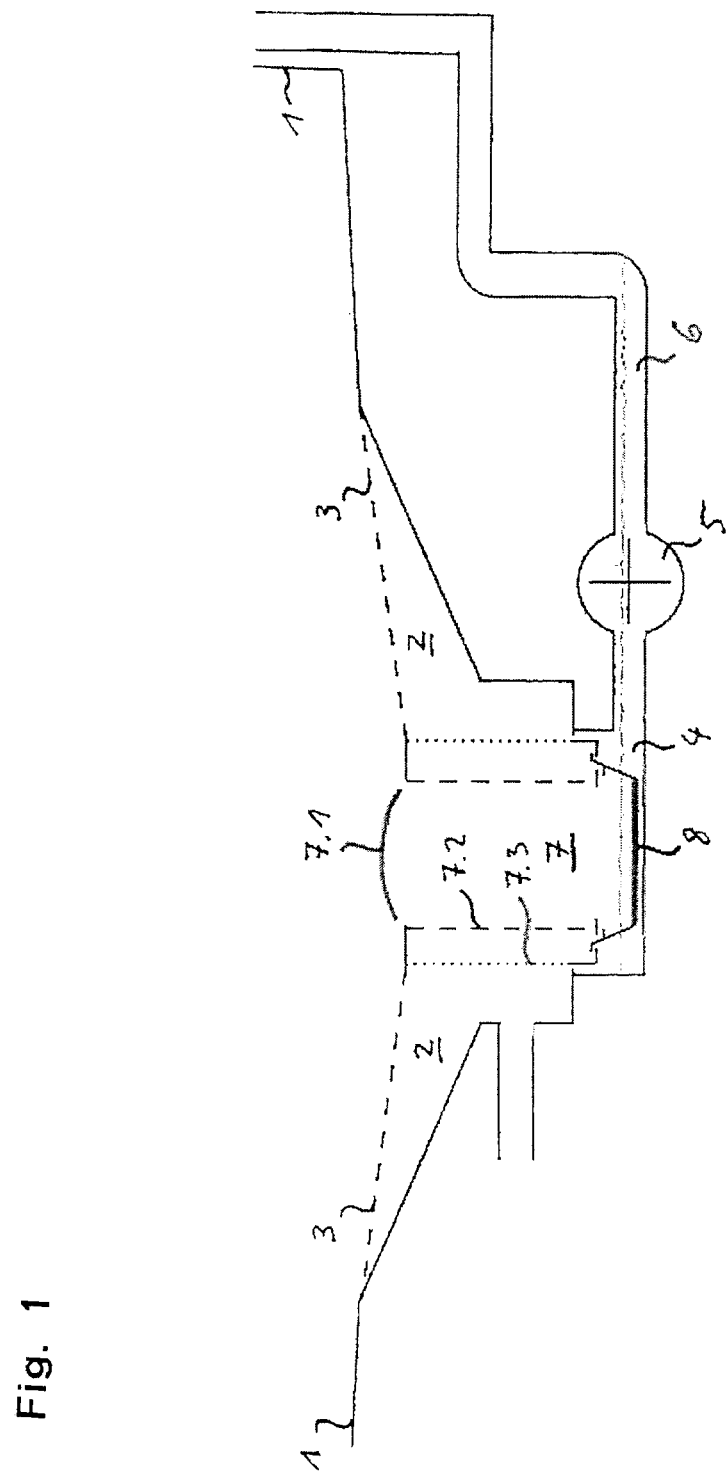

The present invention relates to a liquid-bearing domestic appliance, in particular a domestic dishwasher.

Inside domestic appliances operated with liquid, after an operating cycle there may be liquid leftovers. During prolonged stops the growth of bacteria, fungi or other microbial species may be possible especially in these liquid-covered areas. This may also lead to the emission of bad smell. In particular with dishwashers, this problem is mainly caused by stagnant water remaining in the sump of the dishwasher's tub also after drainage. This water often is mixed with soil residuals, which supports the growth of bacteria or fungi. In the worst case this may lead to slime covers in the sump which can only be removed by scrubbing and emit bad smell.

It is therefore an object of the present invention to provide an appliance having special properties to overcome the aforementioned disadvantages.

According to the present invention the above object is achieved by providing at least part of a liquid-bearing domestic appliance, in particular a domestic dishwasher, with at least one antibiotic agent.

The liquid flowing through the domestic appliance in general is a rinsing liquid which is used to wash dirt off the components put inside the domestic appliance. The rinsing liquid may be clear water or water mixed with rinse agent, rinse aid, salt or the like, as well as any other useful liquid for a washing process.

The antibiotic agent, in the following also referred to as antimicrobial agent, is used to manage what is usually called control of growth. Control of growth means to prevent growth of microorganisms, in particular bacteria, fungi or algae. This control is achieved by killing microorganisms or by inhibiting growth of microorganisms. Control of growth usually involves the use of physical or chemical agents, which either kill or prevent the growth of microorganisms. Agents that kill cells are called cidal agents. Agents that inhibit the growth of cells without killing them are referred to as static agents. Thus the term bactericidal or fungicidal refers to killing bacteria or fungi and bacteriostatic refers to inhibiting the growth of bacteria cells.

By preventing or inhibiting bacteria, fungi or algae growth, the formation of unsavoury and in a worst case unhealthy depositions and bad smells in the domestic appliance can be prevented.

In accordance with a preferred embodiment of the present invention at least one antibiotic agent is provided inside the domestic appliance, in particular in and/or on and/or near wetted areas inside and/or on an inner surface of the domestic appliance.

That the antibiotic agent is provided in or on or near these areas in this context (and in the following) means, that it is directly located there and can be effective from that place or that it may at least reach these areas.

Preferably, the at least one antibiotic agent is provided in and/or on and/or near areas inside the domestic appliance located in stagnant liquid.

As stagnant or leftover liquid is often mixed with organic residuals, the growth of bacteria, fungi or algae may be stronger in these areas. Providing an antibiotic agent in places of stagnant liquids may have the further advantage that it can freely move into the liquid and the antibiotic, in particular static or cidal, effect will affect the whole mass of the liquid and will not only be restricted to a surface.

A localised use of antibiotic agents also grants good cost performances. Therefore, an object can be to focus the use of the antibiotic agent to some sensitive spots in which small amounts the agent have great effectiveness. Besides keeping costs down, this in some cases also avoids heavy mixing of plastics with antibiotic fillers and therefore favours recyclability.

Preferably, at least part of a rinsing tub and/or at least part of a sump being part of the rinsing tub or connected to the rinsing tub, and/or at least part of at least one insert inside the domestic appliance are/is provided with at least one antibiotic agent. Inserts may be dish baskets and/or spraying arms and/or sieve systems or filters and the like. Stagnant liquid mainly remains in the sump and/or outlet and/or pipes of the domestic appliance, were the rinsing liquid is collected and lead away. Therefore, the antibiotic agents preferably will at least be provided in this area. But there may also be some liquid leftovers in other parts of the appliance, e.g. parts of an inserts or the rinsing tub, where antibiotics are advantageous to prevent growth of microorganisms.

In a preferred embodiment of the liquid-bearing domestic appliance according to the present invention at least one antibiotic agent is provided on part of the surface of the rinsing tub and/or the sump and/or the insert.

Preferably, at least one antibiotic agent is at least part of a surface coating, in particular a foil and/or a fabric and/or a synthetic resin and/or a paint and/or a varnish and/or a lacquer. The antibiotic agent may be mixed with the paint, lacquer, synthetic resin, etc. or raw materials for the foil or fabric. With another embodiment of the invention, the antibiotic agent itself may form a surface coating or may form one of several coating layers on the surface.

In accordance with the present invention the at least one antibiotic agent may also be part of a construction material, in particular a resin composition and/or a plastic composition and/or a fabric, of the tub and/or the sump and/or at least one insert. In this case the agent may be incorporated by mixing it with the raw material or one of the raw materials before forming processes such as e.g. extruding or co-extruding or moulding, in particular injection moulding or rotation moulding, and/or subsequent thermoforming etc.

Construction materials may be all kinds of plastics like or on the basis of polyethylene (PE), polypropylene (PP), polyesters (PES), polyamides (PA), polystyrene (PS), acrylic polymers or nylons, including copolymers and/or mixtures or compounds or derivatives with substituents of such polymers, in particular for improvement of certain properties such as impact, chemical or heat resistance for instance, such as HIPS (High Impact Poly Styrene) or ABS and/or preferably thermoplastics, elastomers and/or resins.

With a further advantageous embodiment of the present invention at least one antibiotic agent is provided inside or on the surface of at least one replaceable or removable component which can be fixed or is fixed inside the rinsing tub or the sump. In this case the antibiotic agent can be provided in a very small amount which may also be very cost effective. If necessary, for example if the antibiotic agent is used up or the amount of antibiotic has been insufficient, there can be put a new or an additional antibiotic-bearing component inside the domestic appliance. Furthermore, the parts of the domestic appliance are recyclable without any problem after simply taking out the removable antibiotic-bearing component.

The at least one antibiotic agent preferably comprises at least one bacteriostatic and/or at least one bacteriocidal and or at least one fungicidal and/or at least one anti-algal substance.

In particular, the antibiotic agent preferably comprises at least one of the elements silver or copper or zinc or mercury or tin or lead or bismuth or cadmium or chromium or thallium and/or at least one of the ions thereof, i.e. ions of one or more of the aforementioned elements silver, copper, zinc, mercury, tin, lead, bismuth, cadmium, chromium or thallium. With one special embodiment the antimicrobial agent comprises silver ions and/or copper and/or zinc. Furthermore the agent may comprise any other known antimicrobial substance.

Especially silver has proven to be an excellent bacteriostatic agent and it can be effectively used when bacteria get in contact with ions. It is also preferred that silver is put in contact with stagnant liquid remaining inside the domestic appliance, e.g. in the sump, and silver static effectiveness will be thus used all inside the liquid mass, because ions will be able to move and block bacteria inside it.

In accordance to a preferred embodiment of the present invention the antibiotic agent comprises a ceramic matrix, in particular a natural and/or synthetic zeolite matrix, bearing the at least one bacteriostatic and/or at least one bacteriocidal and or at least one fungicidal and/or at least one anti-algal substance. The so-called antimicrobial filler may be incorporated in a surface coating or a construction material ore applied on a surface of a component, insert or the wall of the rinsing tub and/or the sump of the domestic appliance. The antibiotic substances are then given out of the ceramic matrix by means of ion exchange.

For the antibiotic agent and/or its carrier matrix and/or the construction material and the production, application and composition thereof in particular any of the known embodiments of the following documents U.S. Pat. No. 2,245,737, EP 0 270 129 B1, EP 0 288 063 B1, WO 02/40180 A1, WO 99/47595 A1, US 2001/0000097 A1, WO 00/64259 A1, U.S. Pat. No. 6,187,456 B1 can be used which are incorporated into the disclosure of this application by reference.

EXAMPLE

Tests have run to verify the bacteristaticity of sanitized BC A 21-41 silver ions in ceramic matrix. Thin polystyrene bars have been blended with bacteriostatic. Polystyrene suits this type of application since it is hygroscopic and its polymeric matrix grants good migration of silver ions. Those bars were bent in rings and put inside a rim in the very bottom of the sump of a domestic dishwasher and inside a filter, between net and cylindrical metallic filter.

For the test two dishwashing machines were used. Some water always remains in the sump after last draining. The water was left there and bacteriostatic rings were put in one of the two machines. During a time span of 14 days the air inside the tub was smelt and the results compared.

The dishwasher without bacteriostatic agents emitted a smell like rotten organic materials. Slime grown in the sump was persistent also after one washing cycle and could only be removed by scrubbing. Slime was also found onto the filter net. The dishwasher with bacteriostatic agents smelt of stagnant water but not of rotten. Slimy moulds were not present in the sump or on the filter.

When run another cycle with both dishwashers, it could be noticed, that mould grown into the one without bacteriostatic did resist to an intensive washing. This means that even with a really tough cycle the sump won't come back as before.

The sump with bacteriostatic was then left filled with a more than normal water level about two month. Within this period only a thin layer of slime grew into it, but not of the grade as it has been the case with the machine without the bacteriostatic agent.

At least part of the liquid-bearing domestic appliance of the invention, in particular of the domestic dishwasher, may be provided with at least one antibiotic agent. The at least one antibiotic agent may be provided inside the domestic appliance, in particular in and/or on and/or near wetted areas inside and/or on an inner surface of the domestic appliance. The at least one antibiotic agent may be provided in and/or on and/or near areas inside the domestic appliance which are located in stagnant liquid. At least a part of a rinsing or washing tub of the domestic appliance may be provided, at least at its surface, with at least one antibiotic agent. At least a part of a sump and/or outlet and/or outlet tube of the domestic appliance may be provided, at least at their/its surface(s), with at least one antibiotic agent. At least a part of at least one insert inside the domestic appliance may be provided, at least at its surface, with at least one antibiotic agent, wherein the insert may in particular be a dish basket or a spraying arm or a sieve system or a filter. At least one antibiotic agent is provided on part of the surface of the rinsing tub and/or the sump and/or outlet and/or outlet tube and/or the insert, wherein the at least one antibiotic substance may be at least part of a surface coating or layer, in particular a foil and/or a co-extruded or co-laminated layer and/or a fabric and/or a synthetic resin and/or a paint and/or a varnish and/or a lacquer. The at least one antibiotic agent may be part of a construction material, in particular a resin composition and/or a plastic composition and/or a fabric, preferably of the tub and/or the sump and/or outlet and/or outlet tube and/or or at least one insert. At least one antibiotic agent may be provided in or at at least one replaceable component which can be fixed or is fixed inside the rinsing tub or the sump and/or outlet and/or outlet tube and/or the insert. The at least one antibiotic agent may comprise at least one bacteriostatic and/or at least one bacteriocidal and or at least one fungicidal and/or at least one anti-algal substance. The anti-biotic agent may comprise at least one of the elements silver or copper or zinc or mercury or tin or lead or bismuth or cadmium or chromium or thallium and/or at least one of the ions thereof, in particular silver ions and/or copper and/or zinc. The antibiotic agent may comprise a ceramic matrix, in particular a natural and/or synthetic zeolite matrix, bearing the at least one bacteriostatic and/or at least one bacteriocidal and/or at least one fungicidal and/or at least one anti-algal substance.

In accordance with a further preferred embodiment of the invention, the replaceable or removable component, which can be fixed or is fixed inside the rinsing tub or the sump is a replaceable component of the invention for a liquid-bearing domestic appliance according to claim 1. Favourable embodiments of the replaceable component of the invention are provided according to the dependent claims 2 to 17.

The replaceable component of the invention may be preferably provided with fixation means for replaceable fixation thereof in an area of the liquid-bearing domestic appliance, which contains stagnant water after drainage. Preferably, the fixation means allow the replaceable fixation of the replaceable component within the sump, an outlet or the outlet tube of the appliance, e.g. dishwasher. In particular, the replaceable component may be replaceably fixable by fixation means to the lower face of the flat filter covering the sump of a dishwasher or preferably to the bottom face of a cylindrical filter arrangement arranged within the sump.

In accordance with a still further preferred embodiment of the invention, a liquid-bearing domestic appliance of the invention according to claim 18 is provided. Favourable embodiments of the liquid-bearing domestic appliance of the invention are provided according to the dependent claims 19 to 24.

Figure 2:
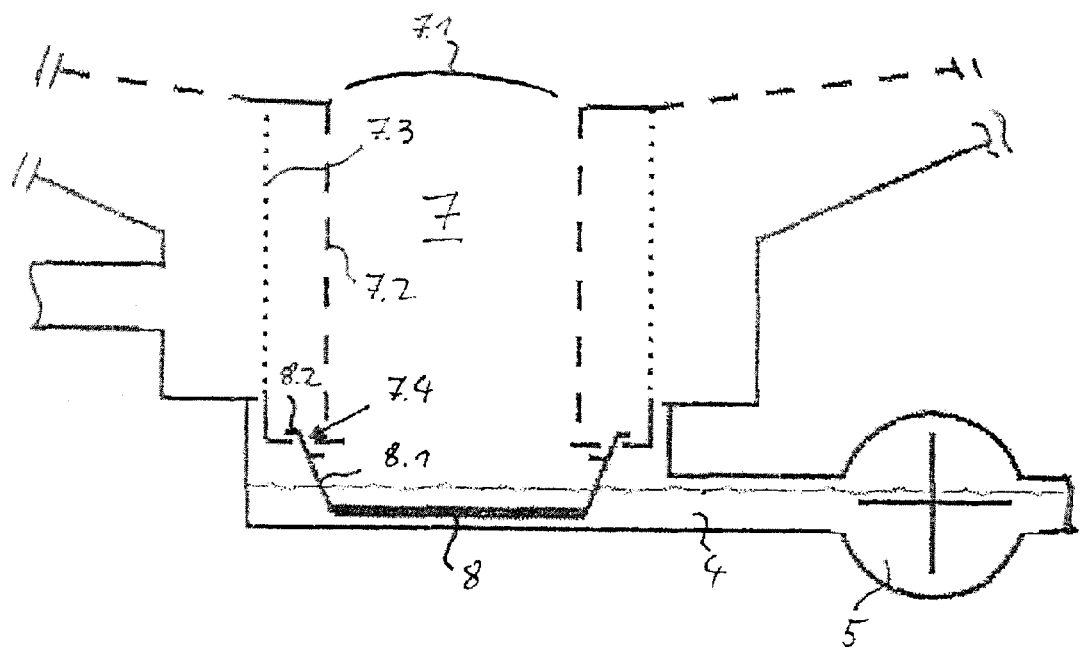

In the following, preferred embodiments of the invention will be explained in more detail referring to the accompanying schematic drawing, however without any limitation of the scope of the invention. The schematic drawing shows in FIG. 1 a sectional view of a lower interior part of a dishwasher of the invention;

FIG. 2 an enlarged detail of FIG. 1

Figure 3:
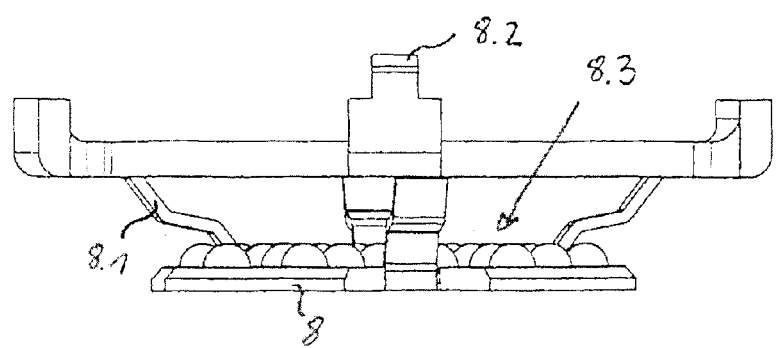
Figure 4:
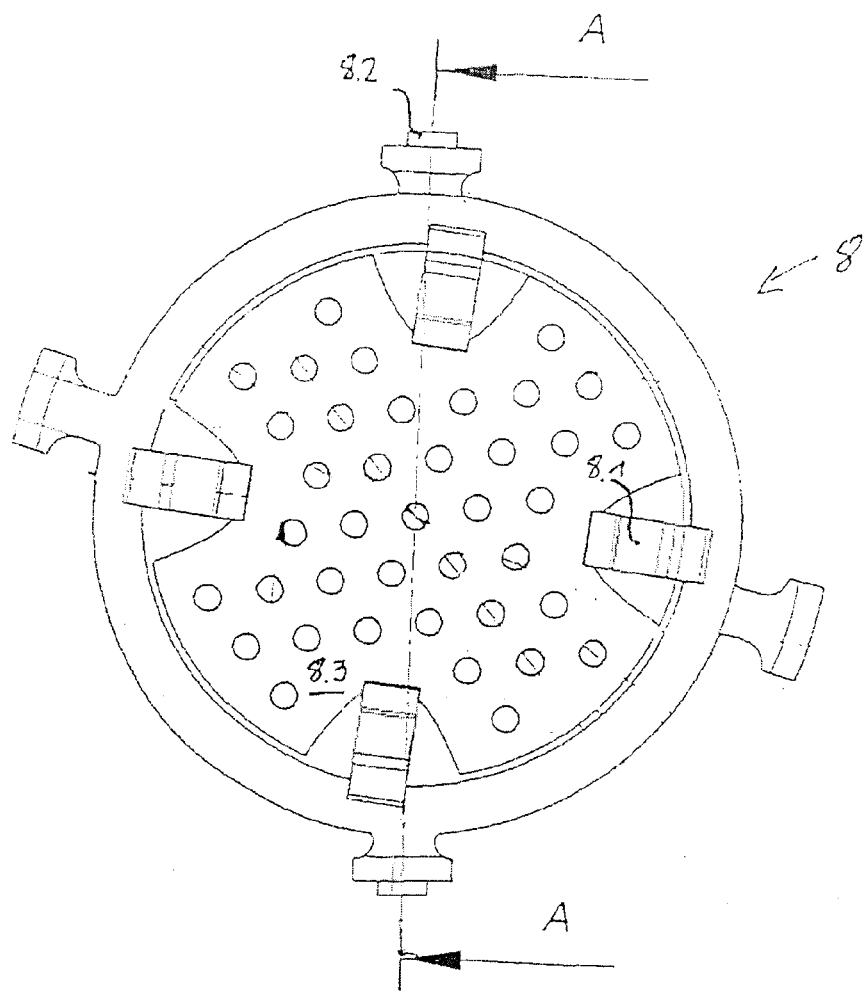
Figure 5:
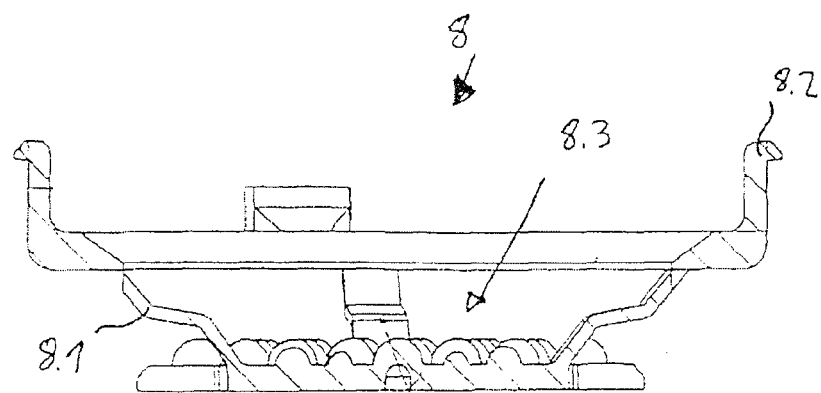

FIG. 3 a side view of the replaceable component of the invention;

FIG. 4 a top view of the replaceable component in FIG. 3;

FIG. 5 a sectional view of the replaceable component along the axis A-A in FIG. 4.

FIG. 1 shows a lower part of the tub 1 of a dishwasher of the present invention, comprising the sump 2, which is covered by the flat filter 3. The sump comprises sidewalls, which are contiguous with the tub, and an outlet 4 at its bottom, which communicates via the drain pump 5 with the outlet tube 6. A cylindrical filter arrangement 7.1, 7.2, 7.3, which comprises a large mesh filter 7.1, a cylindrical fine mesh filter 7.2 and a very fine mesh filter 7.3, is arranged inside the sump. The cylindrical filter arrangement comprises a replaceable component 8, which is arranged in the lower part of the sump, within the outlet.

As can be seen best in FIG. 2, the replaceable component 8 is replaceably fixed to the cylindrical filter arrangement 7. The sanitary component comprises arms 8.1 which carry the fixation means 8.2 at their ends. The fixation means are releaseably inserted into fixation openings 7.4 at the bottom of the cylindrical filter arrangement 8, thereby replaceably fixing the replaceable component 8 to the bottom of the cylindrical filter arrangement 7. Thus, the sanitary component 8 is arranged in the stagnant water, which is indicated in FIGS. 1 and 2 schematically by a low water level, wherein air has entered the drain pump. It can be seen that water can flow above and below the disk-spaped replaceable component 8.

FIG. 3 shows an embodiment of the replaceable component 8 of the invention, which comprises the arms 8.1 and the fixation means 8.2, wherein the fixation means are not located directly at the end of the arms 8.1. The disk-shaped replaceable component 8 comprises an enlarged surface area 8.3 on its upper surface, which enables an enhanced contact of the antibacterial agent comprised in the replaceable component with water that streams over the upper surface of the replaceable component. For simplicity reasons, only one type of structure and only one structure pattern is shown in FIG. 3. Also for simplicity, the replaceable component shown in FIG. 3 only comprises a an enhanced surface area 8.3 on its upper surface, which of course also be formed on the lower surface of the disk-shaped replaceable component 8. The FIGS. 4 and 5 show the replaceable component 8 in more detail.

The invention claimed is:

1. A liquid-bearing domestic appliance comprising a dishwasher with a rinsing tub and a sump, the appliance comprising a sieve system covering the sump and a filter disposed below the sieve system, which is provided with at least one consumable antibiotic agent at or adjacent to at least one surface of the filter, the appliance further comprising a replaceable component with at least one support arm that supports an enlarged surface area that is engaged with said at least one consumable antibiotic agent inside or on said enlarged surface area, and wherein the replaceable component is suspended below the filter by said at least one support arm and is arranged inside an area of the liquid-bearing domestic appliance so that both of the enlarged surface area and the consumable antibiotic agent are directly exposed to a rinsing liquid and stagnant water after drainage, including inside a lower part of the sump, an outlet and/or an outlet tube, and wherein the replaceable component is fixed replaceably by at least one fixation means that is releasably inserted into a corresponding fixation opening at a bottom of the filter via said at least one support arm such that the replaceable component is configured to be periodically removed from said filter and replaced as said at least one consumable antibiotic agent is consumed over time from said enlarged surface area via exposure to the rinsing liquid and/or stagnant water.

2. The liquid-bearing domestic appliance according to claim 1, wherein the at least one antibiotic agent comprises at least part of a surface of the filter, wherein the antibiotic agent is a foil and/or a co-extruded or co-laminated layer and/or a fabric and/or a synthetic resin and/or a paint and/or a varnish and/or a lacquer.

3. The liquid-bearing domestic appliance according to claim 1, wherein the at least one anti-biotic agent comprises at least one bacteriostatic and/or at least one bacteriocidal and/or at least one fungicidal and/or at least one anti-algal substance.

4. The liquid-bearing domestic appliance according to claim 3, wherein the antibiotic agent comprises at least one of the elements silver or copper or zinc or mercury or tin or lead or bismuth or cadmium or chromium or thallium, and/or at least one of the ions thereof.

5. The liquid-bearing domestic appliance according to claim 3, wherein the antibiotic agent comprises a ceramic matrix, a natural zeolite matrix and/or synthetic zeolite matrix, bearing the at least one bacteriostatic and/or at least one bacteriocidal and/or at least one fungicidal and/or at least one anti-algal substance, wherein the antibiotic agent comprises a ceramic matrix comprising silver and/or silver ions.

6. The liquid-bearing domestic appliance according to claim 1, wherein the sieve system and the filter are located below the rinsing tub.

7. The liquid-bearing domestic appliance according to claim 1, wherein the at least one support arm carries the fixation means.

8. The liquid-bearing domestic appliance according to claim 7, wherein said at least one arm carries the fixation means at an end of said at least one arm.

9. The liquid-bearing domestic appliance according to claim 7, wherein said at least one arm carries the fixation means at a location spaced apart from an end of said at least one arm.

10. The liquid-bearing domestic appliance according to claim 1, wherein the replaceable component comprises a plurality of support arms each carrying fixation means.

11. The liquid-bearing domestic appliance according to claim 1, wherein the replaceable component carrying the at least one antibiotic agent is provided inside an area of the liquid-bearing domestic appliance that is spaced apart from the rinsing tub.

12. The liquid-bearing domestic appliance according to claim 1, wherein the replaceable component has the shape of a disk and is adapted to be accommodated between a bottom of the filter and a bottom of the sump, such that washing liquid can pass above and below the replaceable component.

13. The liquid-bearing domestic appliance according to claim 1, wherein the replaceable component can be replaced when said at least one consumable antibiotic agent is reduced to an amount that is insufficient to inhibit bacterial growth in the sump, outlet, and/or outlet tube of the liquid-bearing domestic appliance.

14. The liquid-bearing domestic appliance according to claim 1, wherein said replaceable component comprises said at least one consumable antibiotic agent as a layer on said enlarged surface area.

15. The liquid-bearing domestic appliance according to claim 1, wherein said at least one support arm comprises a projection that removably interengages with said filter so that the replaceable component is fixed replaceably inside the sump, outlet, and/or outlet tube of the liquid-bearing domestic appliance.

* * * * *